United States Patent [19]
Tsoukas et al.

[11] Patent Number: 5,993,812
[45] Date of Patent: Nov. 30, 1999

[54] METHOD OF DELAYING THE PROGRESSION OF AN INFECTION WITH THE HUMAN IMMUNODEFICIENCY VIRUS

[75] Inventors: Christos M. Tsoukas, Montreal; Barry Michael Woloski, Winnipeg, both of Canada

[73] Assignee: Cangene Corporation, Winnipeg, Canada

[21] Appl. No.: 08/835,400

[22] Filed: Apr. 7, 1997

Related U.S. Application Data

[63] Continuation-in-part of application No. 08/713,765, Sep. 13, 1996, abandoned.
[60] Provisional application No. 60/003,756, Sep. 14, 1995.
[51] Int. Cl.$^6$ .............................. A61K 39/395; C07K 1/00
[52] U.S. Cl. .................. 424/130.1; 530/350; 530/388.7; 424/142.1; 424/141.1; 424/153.1
[58] Field of Search .............................. 424/130.1, 153.1; 530/350, 388.7

[56] References Cited

FOREIGN PATENT DOCUMENTS

WO9505196  2/1995  WIPO .

OTHER PUBLICATIONS

Hamilton, et al, "The Many Personalities of Gene–Spliced Drugs" Business Week, Jul. 30, 1990 p. 68, No. 3171.
Oksenhendler, et al, "Anh–Rh Immunoglobulin Therapy . . . " Blood 71:1499–1502, 1988.
Brunkhorst et al., Infection 18:28–32, 1990.
Coyle et al., Changes in theLymphocyte Count and Lymphocyte Subsets After Splenectomy in Human Immunodeficiency Virus Infection, Letters and Correspondence, pp. 144–146.
DeSimone et al., Immunopharma. and Immunotoxic., 13:447–458, 1991.
Gringeri et al., British Journal of Haemotology, 80:337–340, 1992.
Güngör et al., Eur. J. Pediatr., 152:650–654, 1993.
Mofenson and Moye, Pediatric Research, 33:80–S89, 1993.
Mofenson et al., Journal of Acquired Immune Deficiency Syndrome, 6:1103–1113, 1993.
Schrappe–Bächer et al., Vox Sang, 59:3–14, 1990.
Shearer et al., Ann. N.Y. Acad. Sci., pp. 35–51.
Wagner et al., Arch. of Disease in Childhood., 67:1267–1271, 1992.
Watson, et al., "Recombinant DNA", *Scientific American Books*, Chapter 25.
Okesenhendeler, et al., "Anti–RH immunoglobulin therapy for human immunodeficiency virus–related immune thrombocytopenic purpura", *Blood*, 71 (5) 1499–502.

*Primary Examiner*—Frank C. Eisenschenk
*Assistant Examiner*—Brett Nelson
*Attorney, Agent, or Firm*—Merchant, Gould, Smith, Edell, Welter & Schmidt

[57] ABSTRACT

Therapeutic and prophylactic methods using Rh antibodies for delaying the progression of infection with the Human Immunodeficiency Virus (HIV) in a subject who is exposed to HIV, or infected by HIV.

13 Claims, 12 Drawing Sheets

METHOD OF DELAYING THE PROGRESSION OF AN INFECTION WITH THE HUMAN IMMUNODEFICIENCY VIRUS

This is a Continuation-in-Part of U.S. patent application Ser. No. 08/713,765, filed Sep. 13, 1996 now abandoned, which claims priority from U.S. Provisional Aplication No. 60/003,756 that was filed on Sep. 14, 1995.

BACKGROUND OF THE INVENTION

Acquired Immunodeficiency Syndrome (AIDS) is a transmissible disease caused by a retrovirus. The retrovirus responsible for AIDS was first identified by Barre-Sinoussi, F., et al, Science 220, 868–871, 1983 and Gallo, R. C., et al., Science 224:500–503, 1984, and related retroviruses have been isolated from patients in different areas. The accepted terminology for these isolates is human immunodeficiency virus (HIV), which has subtypes e.g. HIV type-1 and HIV type-2.

HIV produces a slow but usually progressive deterioration in the host immune system. Primary HIV infection represents the initial stage of AIDS when there is a burst of viral replication associated with dissemination in lymphoid tissue (Piatak et al, 1993, Science 1988, 239:586; Daar et al, 1991, N. Eng. J. Med. 1991, 324:961–964; and Fauci, 1993, Science 1993, 262:1011–1018). This acute HIV infection is largely an asymptomatic infection with a persisting generalized lymphadenopathy. A second stage in AIDS is a symptomatic HIV infection complicated by conditions attributable to compromised cellular immunity (e.g. thrush, listerosis, peripheral neuropathy). The third stage in AIDS is defined by laboratory criteria (reduced CD4+ cell numbers of percentage of total lymphocytes) and clinical criteria (characteristic opportunistic infections, neoplasms, central nervous systems disorders, and cachexia). Typically acute HIV infection lasts about 12 weeks; there is a period of clinical latency that lasts 5 to 10 years, and the patient survives about 2 years after a diagnosis of AIDS can be made. There is a progressive decrease in the number of CD4+ cells, as well as the destruction of CD4+ cells during these periods of the HIV infection (Hoxie, 1995, In Hoffman, R., et al., eds. Hematology. Basic Principles and Practice. Second Edition. New York. Churchill Livingstone, 1995:2011–2019).

The mechanisms by which HIV infection produces immunodeficiency is the subject of intensive investigations. It has been suggested that the decrease in CD4+ lymphocyte number and function involves direct effects of viral infection on mature and progenitor CD4 cells, as well as the destruction by cellular or humoral mechanisms of uninfected CD4 cells that display absorbed or processed viral antigens on their surface. Monocytes and macrophages which express the CD4 antigen are also targets for HIV infection. These cells of the reticuloendothelial system probably represent a major reservoir for virus production in vivo (Gendelman et al., 1989, AIDS 2:475; Embretson et al, 1993, Nature 362:359). Monocytes play a central role in the processing and presenting of antigens to T and B lymphocytes and they are able to migrate to the central nervous system. Therefore, infection of monocytes by HIV may play a role in the development of both immunologic and neurologic disease in infected individuals.

The use of intravenous immunoglobulin in the treatment of patients with HIV infections has been widely documented (See Schrappe-Bacher, M., Vox-Sang, 1990; Suppl 1:3–14; Wagner, N., et al. Arch. Dis. Child. 1992, Oct., 67(10): 1267–71; Brunkhorst, U. et al., Infection, 1990, 18(2):86–90; De Simone, C., et al, Immunopharmacol Immunotoxicol. 1991 13(3) 447–58; Gungor, T. et al., Eur. J. Pediatr., 1993 152(8): 650–4; Mofenson, L. M. et al., J. Acquir. Immune Defic. Syndr. 1993, 6(10): 1103–13; Mofenson, L. M. and Moye, J, Pediatr. Res. 1993 33(I Suppl): S80–7; discussion S87–9; Ersoy et al., Turk. J. Pediatr. 1992 34(4): 203–9; Shearer, W. T. et al, Ann N.Y. cad. Sci. 1993, 693:35–51; and WO 89/01339 to Cummins et al.). Intravenous immunoglobulin administration has been reported to be beneficial in reducing the rate of secondary opportunistic bacterial or viral infections in HIV-positive adults and children. It has also been reported to temporarily increase and/or maintain CD4+T-lymphocyte profiles in HIV-infected patients. However, this activity has not been consistently observed.

The serologic and immunologic effects of intravenous immunoglobulin on T-cell count appear to be dependent upon both the severity of the HIV infection and the duration of the study. Previous studies on the effect of intravenous immunoglobulin activity on CD4+ cell count and clinical efficacy were conducted in patients with early HIV infection (entry cell counts of $\geq 200/mm^3$) using relatively short treatment periods ($\leq 16$ months). In contrast, serologic effects diminish with advancement of HIV infection (e.g. in patients with AIDS-related complex), and intravenous immunoglobulin was demonstrated to be serologically and clinically ineffective at 24 months. Therefore, the serological effects of intravenous immunoglobulin cannot solely account for its clinical actions, and the long-term benefits of intravenous immunoglobulin in HIV infections remains to be established.

Immune thrombocytopenia purpura (ITP) is a common complication of HIV infection. It can occur at any stage of its natural history, both in patients diagnosed with AIDS, those with AIDS-related complex, and those with HIV infection but without AIDS symptoms. ITP secondary to HIV infection involves both reduced production of platelets and antibody-mediated destruction of platelets by the reticuloendothelial system.

Rh(D) immunoglobulin has been used to treat HIV-associated ITP in adults and children (Gringeri, A., et al., Br. J. Haematol. 1992 80(3): 337–40; Rossi, E., et al., Haematologica 1991 76(2): 141–9; Landonio, G., et al., AIDS 1990 4(1): 29–34; Brusamolino, E., et al., Haemotologica 1989 74(1): 51–6; Cattaneo, M., et al., Blood 1989 73(1): 357); and Bussel et al., Blood, 1991, 77:1884–1893). The majority of patients treated with Rh(D) immunoglobulin respond with increased platelet counts, but the platelet response is temporary and lasts about 3 weeks. Rh(D) immunoglobulin treatment has been ineffective in Rh negative patients, and in all patients that have received a splenectomy prior to therapy.

PCT/US94/08312 (published on Feb. 23,1995 as No. WO 95/05196) describes a method for slowing the progression of HIV infection in patients by providing individuals with Rh antibody-antigen complexes or Rh antibody-antigen-complement complexes to inhibit binding of HIV-antibody complexes to follicular dendritic cells in lymph node tissue. However, one would not expect that these complexes would have the reported inhibitory effect since antibody complexes administered extraneously are not able to enter the lymphatic compartment to elicit the effect.

SUMMARY OF THE INVENTION

The present inventors have found that Rh antibodies delay the progression of infection with the Human Immunodeficiency Virus (HIV). Patients treated with Rh antibodies had stable CD4+ counts over a much longer period than would be normally expected. Progression of the disease is delayed in subjects with or without ITP secondary to the HIV infection.

Broadly stated the present invention relates to a method for delaying the progression of infection with HIV in a subject who is exposed to HIV, or infected by HIV, comprising administering an amount of Rh antibodies sufficient to delay the progression of the infection. In preferred embodiments of the invention an Rh positive subject is treated with anti-Rh$_o$(D), and an Rh negative subject is treated with anti-c.

The invention also relates to a pharmaceutical composition for use in delaying the progression of an infection with HIV in a subject who is exposed to HIV, or infected by HIV, comprising Rh antibodies in an amount sufficient to delay the progression of the infection. In preferred embodiments of the invention the pharmaceutical compositions contain anti-Rh$_o$(D) or anti-c.

Still further the invention contemplates the use of Rh antibodies, preferably anti-Rh$_o$(D), for delaying the progression of infection with Human Immunodeficiency Virus (HIV) in a subject who is exposed to HIV, or infected by HIV, and the use of Rh antibodies for manufacturing a medicament for delaying the progression of infection with Human Immunodeficiency Virus (HIV).

These and other aspects of the present invention will become evident upon reference to the following detailed description and attached drawings. In addition, reference is made herein to various publications, patents and patent applications which are hereby incorporated by reference in their entirety.

DESCRIPTION OF THE DRAWINGS

The invention will be better understood with reference to the drawings in which.

DETAILED DESCRIPTION OF THE INVENTION

Figure 1:
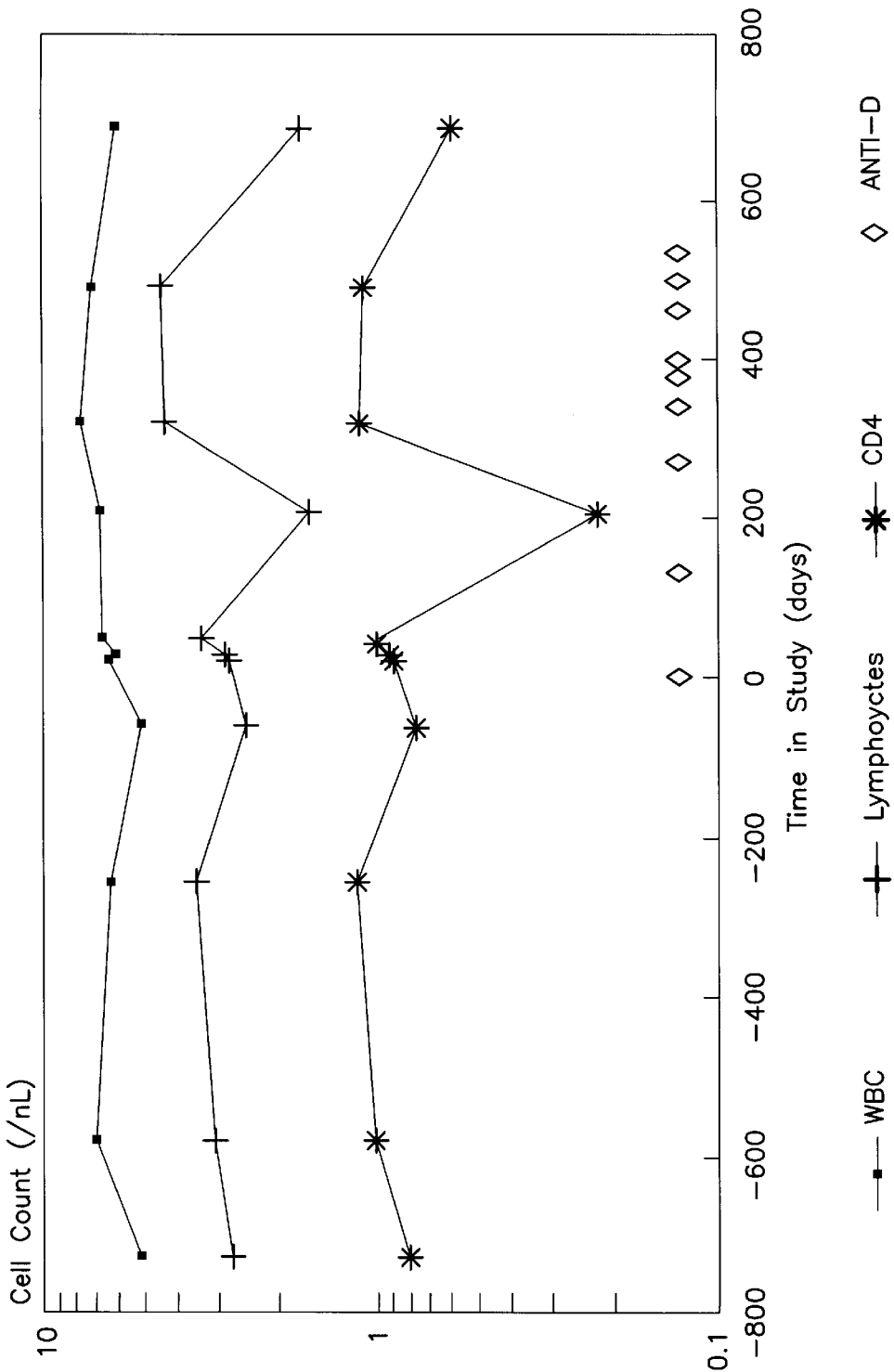
FIG. 1 is a graph showing white cell counts (including CD4+) versus time after enrollment of patient BI-107 in the study of intravenous anti-Rh$_o$(D) therapy.

As hereinbefore mentioned, the present inventors have found that Rh antibodies, in particular anti-Rh$_o$(D), delay the progression of infection with HIV. In particular, the present inventors have found that patients with HIV infection that have been treated with anti-Rh$_o$(D) have CD4+ counts that are stable over long periods of time. While not wishing to be bound by a particular theory, the Rh antibodies act by interfering with the interaction of the HIV with the cellular immune system. Treatment with Rh antibodies results in red blood cell clearance which induces reticuloendothelial blockage which is seen primarily as an action on the splenic macrophages and other monocytes/macrophages. These effects on the reticuloendothelial system may attenuate transmission of HIV to circulating T lymphocytes by a reservoir of infected splenic macrophages. The effect of anti-Rh$_o$(D) treatment is similar to an apparent delay of CD4+ cell decline observed in HIV-1 patients following splenectomy. The Rh$_o$(D) antibodies may also effect cytokines resulting in cytopathic effects.

The methods, compositions and uses of the invention, use Rh antibodies. Within the context of the present invention, Rh antibodies are understood to include antibodies specific for antigens of the Rh blood group system, or epitopes thereof. (See The Rh Blood Group System, in Blood Transfusion in Clinical Medicine., ed. Mollison PL et al., chapter 8, page 328, for a review of the Rh blood group antigens, which is incorporated in its entirety herein by reference). Examples of Rh antibodies include anti-D (also known as anti-Rh$_o$, and also referred to herein as anti-Rh$_o$(D)); anti-C (also known as anti-rh'); anti-E (also known as anti-rh"); anti-c (also known as anti-hr'); and, anti-e (also known as anti-hr").

Generally Rh antibodies for use in the invention are selected depending on the Rh antigens present/absent on the red cells of the subject to be treated. Anti-Rh$_o$(D) is preferably used to treat Rh positive (i.e. D positive) subjects, and anti-c is preferably used to treat Rh negative (i.e. D negative) subjects.

The Rh antibodies used in the present invention may be preparations from plasma enriched for Rh antibodies, monoclonal antibodies, polyclonal antibodies, antibody fragments (e.g., Fab, and F(ab')$_2$), and recombinantly produced binding partners.

Preparations with a high Rh antibody content may be isolated as an immunoglobulin fraction from plasma, preferably human plasma, using conventional techniques. For example, an Rh IgG fraction may be isolated from human plasma by (a) the Cohn cold ethanol method and modifications thereto (e.g. see Barandun, S., et al., 1962, Vox Sang. 7, 157–174); (b) the DEAE-Sephadex method described by Hoppe, H. H. et al., 1967, Munch. Med. Wochenschr. 109:1749–1752); or (c) the anion-exchange method described in Canadian Patent No. 1,201,063, and modifications thereto. Commercially available Rh immunoglobulin preparations may also be used in the methods, uses and compositions of the invention. For example, anti-$Rh_o$(D) preparations including WinRho®, WinRho SD®, WinRho SDF® (Cangene Corporation, Winnipeg, Canada), and HypRho®-D (Miles Canada Inc., Etobicoke, Canada) may be used in the present invention.

In an embodiment of the invention an $Rh_o$(D) IgG fraction is prepared by contacting an aqueous animal plasma fraction containing IgG with one or more chromatographic separation columns to produce a purified IgG rich fraction. The aqueous animal plasma fraction used in the process may be normal non-immunized plasma from an animal source, preferably a human source, or hyper-immune plasma such as plasma from Rh alloimmunized donors. The plasma is modified to the ionic strength and pH of the initial buffer used with the chromatographic separation column. In an embodiment of the invention, the aqueous animal plasma fraction is contacted with one or more, preferably one or two anionic exchangers to produce a purified IgG rich fraction.

The purified IgG rich fraction may optionally be treated with a solvent and detergent to inactivate lipid envelope viruses. Suitable solvents and detergents which may be used to inactivate lipid envelope viruses include Triton X-100 and tri (n-butyl) phosphate. The solvents and detergent may be removed by conventional methods such as reverse phase chromatography.

The chromatographic separations may be carried out on anion exchangers using the procedure as described in Canadian Patent No. 1,201,063 which is incorporated herein in its entirety by reference. By way of example, the aqueous animal plasma fraction is applied to an anion exchange column which may contain an agarose cross-linked anionic exchange resin such as DEAE-Sepharose CL6B or DEAE-Biogel, and an IgG rich fraction is obtained by elution with an equilibrating buffer. The IgG rich fraction may be concentrated for example by ultrafiltration. The IgG rich fraction is applied to a second different anion exchange column such as DEAE-Biogel™, or Deae-Sephadex™ A-50. A purified IgG rich fraction is isolated by elution with an appropriate equilibrating buffer.

The purified IgG fraction may be formulated with a wetting agent such as Polysorbate 80, also known as Tween 80. The wetting agent reduces the amount of fragmentation over extended periods of time to provide a highly stable preparation enriched for $Rh_o$(D) antibodies. The purified IgG fraction may be further purified using ultrafiltration.

The purified IgG rich fraction obtained using the process described above may be further stabilized by the addition of stabilizers such as mannitol, glycine (e.g. 0.1 M glycine), and sodium chloride (e.g. 0.15 M sodium chloride), and the pH of the fraction may be adjusted within the range 4.0 to 5.4. The resulting preparation may be sterilized for example, by filtration, and it may be used in this form. If desired the preparation may be freeze-dried, and reconstituted using a suitable solution, e.g. 0.9% sodium chloride.

A preferred preparation obtained using the process described above has the following characteristics: 2–3% human immune globulin, no or very low level buffer, essentially no ionic strength, 10 ppm polysorbate 80, 10% sorbitol, pH 4.0.

Rh antibodies used in the present invention may be preparations containing polyclonal antibodies specific for Rh antibodies generated using conventional procedures in humans and animals. By way of example, the $Rh_o$(D) antigen is used to immunize the animal through intraperitoneal, intramuscular, intraocular, or subcutaneous injections, with or without an adjuvant such as Freund's complete or incomplete adjuvant. Following several booster immunizations, samples of serum are collected and tested for reactivity to the antigen in standard assays, examples of which are described below. Particularly preferred polyclonal antisera will give a signal on one of the assays that is at least three times greater than background. Once the titer of the animal has reached a plateau in terms of its reactivity to the antigen, larger quantities of antisera may be readily obtained either by periodic (e.g. weekly) bleedings, or by exsanguinating the animal.

Human Rh antibodies may also be produced in human volunteers. For example, an anti-$Rh_o$(D) preparation may be obtained from a subject initially immunized naturally during an Rh incompatible pregnancy, and given booster immunizations of whole Rh positive red cells.

Monoclonal Rh antibodies may also be readily generated using conventional techniques (see U.S. Pat. Nos. RE 32,011, 4,902,614, 4,543,439, and 4,411,993 which are incorporated herein by reference; see also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference).

Other techniques may also be utilized to construct monoclonal antibodies (see William D. Huse et al., "*Generation of a Large Combinational Library of the Immunoglobulin Repertoire in Phage Lambda,*" Science 246:1275–1281, December 1989; see also L. Sastry et al., "*Cloning of the Immunological Repertoire in Escherichia coli for Generation of Monoclonal Catalytic Antibodies: Construction of a Heavy Chain Variable Region-Specific cDNA Library,*" Proc Natl. Acad. Sci USA 86:5728–5732, August 1989; see also Michelle Alting-Mees et al., "*Monoclonal Antibody Expression Libraries: A Rapid Alternative to Hybridomas,*" Strategies in Molecular Biology 3:1–9, Jan. 1990; these references describe a commercial system available from Stratacyte, La Jolla, Calif., which enables the production of antibodies through recombinant techniques). Similarly, binding partners may also be constructed utilizing recombinant DNA techniques to incorporate the variable regions of a gene which encodes a specifically binding antibody (See Bird et al., Science 242:423–426, 1988).

Monoclonal $Rh_o$(D) antibodies and methods for preparing same which may be used in the present invention are described in WO 91/07492 Canadian Patent Nos. 1,303,533 and 1,303,534, EP 251440 (all to the Central Blood Laboratory Authority); WO 94/00561 (National Reg. Association Transfusion Sanguine/Biotest Pharma GmBH); WO 91/05800 (Foundation Centre National Transfusion Sanguine); EP 523949 (Welcome Foundation), DD 338332 ( Humboldt University, Berlin); GB 2127434 (University of London); JP 60115530 (Wako Pure Chem.); and, SU 1678830 (Research Institute Hematology).

It will be apparent to one skilled in the art that the preparations used in the present invention may contain more than one type of Rh antibody. For example, a preparation may contain anti-$Rh_o$(D) and anti-c.

Compositions/preparations of the invention contain Rh antibodies, either alone or together with other active substances. Such compositions are for intravenous, intranasal, intramuscular, subcutaneous, oral, enteral or parenteral use. In particular, those forms for intramuscular or subcutaneous administration are used, or forms for infusion or intravenous injection are used, which can be prepared as solutions of the antibodies or as powders of the antibodies to be mixed with one or more pharmaceutically acceptable excipients or diluents, suitable for the aforesaid uses and with an osmolarity which is compatible with the physiological fluids. For example, as described herein, an Rh antibody preparation may be formulated with a wetting agent and/or stabilized by addition of a stabilizer. Preferably, the preparations are in a form suitable for intravenous or intramuscular administration (e.g. WinRho SD®, Cangene Corporation, Winnipeg, Canada). When administering the compositions/preparations of the invention by injection, the administration may be by continuous infusion, or by single or multiple boluses.

In an embodiment of the invention forms for intravenous injection or infusion are selected to maximize drug bioavailability, reduce dosage, and to elicit faster pharmacodynamic action i.e. reticuloendothelial blockage. For example, Rh negative subjects were injected with adult and fetal Rh positive red blood cells and subsequently WinRho™ (e.g. 120 µg) was administered by intravenous or intramuscular injection. Peak plasma levels of WinRho™ were achieved immediately after intravenous injection but were only achieved 24 hours after intramuscular injection. Intravenous injection also produced two-fold higher peak plasma levels than intramuscular injection. Clearance of Rh positive red blood cells was complete within 8 hours of intravenous administration, and 24 hours of intramuscular administration (Bowman, J. M., et al., CMA Journal 123:1121–1125, 1980). In the present invention, a faster red blood cell clearance would correspondingly produce a faster reticuloendothelial blockage in delaying HIV disease progression.

The compositions/preparations of the invention may contain one or more Rh antibodies together with one or more other active substances. Examples of active substances which may be used in the compositions/preparations include (i) nucleoside reverse transcriptase inhibitors such as 2',3'-dideoxyinosine (didanosine, ddI, or VIDEX™), 2',3'-dideoxycytidine (zalcitabine, DDC, or HIVID™), 3'-azidothymidine (zidovudine, AZT or RETROVIR™), L(-)-2'.3'-dideoxy-3'-thiacytidine (lamivudine, 3TC or EPIVIR™) and didehydrodideoxythymidine (D4T), (ii) non-nucleoside reverse transcriptase inhibitors such as nevirapine, delavirdine, atevirdine, pyridinones and TIBO derivatives and (iii) protease inhibitors such as saquinavir (INVIRASE™), ritonavir (NORVIR™), indinavir (CRIXIVAN™), and other investigational agents such as acetylpepstatin and pepstatin, A-74704 and A-77003, AG-2 and AG-4, MVY-101, JG-365, L-689502, Ro-31-8588, U-75875 and U-85548e (Erickson, J. W., Annu. Rev. Biochem. 62:543–585, 1993), AG1343, nelfinavir (VIRACEPT™); Agouron Pharmaceuticals, Inc.), VX-478 (141W94) (Vertex Pharmaceuticals Inc./Glaxo Wellcome Co.), secretory leukocyte protease inhibitor (SLPI; National Institute of Dental Research/Synargen, Inc.), KN1-272 (dynostatin) (Nikko Kyoto Pharmaceutical/National Cancer Institute), U-103373 (Upjohn), CGP-53437 (Ciba-Geigy), Hoe/Bay-793 (Hoechst-Bayer), SR-41476 (Sanofi), L-735–524 (MK63a) (Merck & Co.), and ABT-538 (Abbott Laboratories). The Rh antibodies may also be administered in combination with human growth hormone or human interferon. The Rh antibodies and active substances may be administered by any conventional means available for the use in conjunction with pharmaceuticals, either as individual separate dosage units administered simultaneously or concurrently, or in a physical combination of each component in a single or combined dosage unit. The antibodies and active substances can be administered alone, but are generally administered with a pharmaceutical carrier selected on the basis of the chosen route of administration and standard pharmaceutical practice as described herein.

The combination of Rh antibody and active substances may result in a synergistic action which enhances the effects of the Rh antibodies, or enhances the effects of the active substances. The doses of Rh antibodies and active substances may be each selected so that the Rh antibodies and active substances alone would not show a full effect.

The preparations of the invention can be intended for administration to humans or animals. An appropriate preparation may be selected for a particular subject based on the presence/absence of Rh antigens on the surface of the red blood cells of the subject. Generally, Rh positive (i.e. D positive) subjects are treated with anti-$Rh_o$(D), and Rh negative (i.e. D negative) subjects are treated with anti-c. Preferably, the preparations/compositions of the invention are administered to subjects with entry CD4+ cell counts above about 200 cells per $mm^3$.

The compositions/preparations of the invention are intended to provide to the recipient subjects an amount of Rh antibodies sufficient to delay the progression of an HIV infection, and in particular to slow the decline of CD4+ cells in a subject. An amount is said to be sufficient if the dosage, route of administration etc. of the Rh antibodies are sufficient to delay the progression of an HIV infection, and in particular to slow the decline of CD4+ cells and reduce viral burden.

Dosages to be administered depend on individual needs, on the desired effect, and on the chosen route of administration. Daily dosages to humans by intramuscular or intravenous injection generally vary between about 10 µg to 400 µg per kg body weight. For intravenous injection or infusion, the preferred dosage is about 10 to 200 µg per kg body weight. Intravenous dosages which are greater than about 20 µg per kg body weight may be more effective in effecting reticuloendothelial blockage. Preferably the dosage for intravenous injection is about 50 µg per kg body weight. The preferred dosage for intramuscular injection is about 20 µg to 400 µg per kg body weight. These dosages are significantly lower than those suggested for intravenous immunoglobulin treatment of patients with HIV infections. The lower dosages provided in the present invention reduce the risk of adverse reactions such as cardiovascular/thromboembolic events.

To delay HIV progression in asymptomatic HIV patients, multiple courses of Rh antibodies may be given by intravenous injection. In one embodiment, each course may consist of intravenous injection of about 25 µg per kg of body weight for two consecutive days for a total of 50 µg per kg per course. The courses may be give at three week intervals.

The compositions described herein can be prepared by per se known methods for the preparation of pharmaceutically acceptable compositions which can be administered to patients, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the Rh antibodies in association with one or more pharmaceutically acceptable vehicles or diluents, and contained in buffered solutions with a suitable pH and iso-osmotic with the physiological fluids.

Pharmaceutical techniques may also be employed to control the duration of action of the compositions/preparations of the invention. Control release preparations may be prepared through the use of polymers to complex, encapsulate, or absorb the Rh antibodies.

The therapeutic effects of the present invention may be obtained by providing to a patient any of the above described Rh antibody preparations or compositions. The preparations and compositions may be provided to patients who are exposed to, or infected by HIV infection. Therefore, the preparations and compositions of the invention may be administered to patients with AIDS. The term "AIDS" used herein includes the early asymptomatic stages of the disease following infection with HIV-1 and HIV-2, to the advanced symptomatic stages of the disease, for example the stage referred to as AIDS related complex (ARC). The preparations and compositions of the invention may be given to patients with or without the onset of clinically significant ITP, including those under remission from thrombocytopenic episodes. Clinically significant ITP and platelet levels requiring therapeutic intervention are described for example, in George, J. N. et al., Blood 88:3–40, 1996.

Having generally described the invention, the same will be more readily understood through reference to the following example which is provided by way of illustration, and it is not intended to be limiting of the present invention.

EXAMPLES

Example 1

Figure 2:
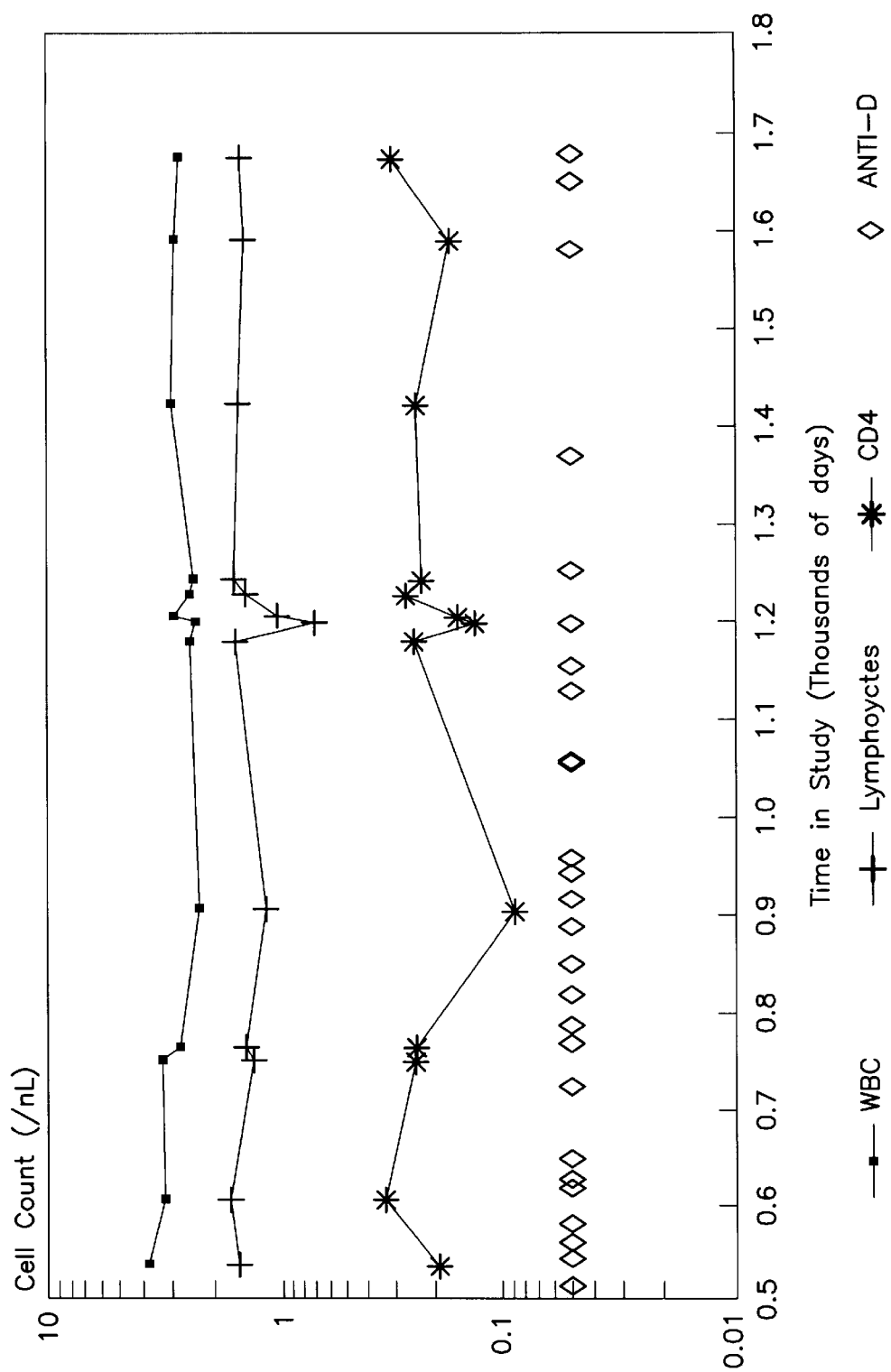
FIG. 2 is a graph showing white cell counts (including CD4+) versus time after enrollment of patient BI-21 in the study of intravenous anti-Rh$_o$(D) therapy.
Figure 3:
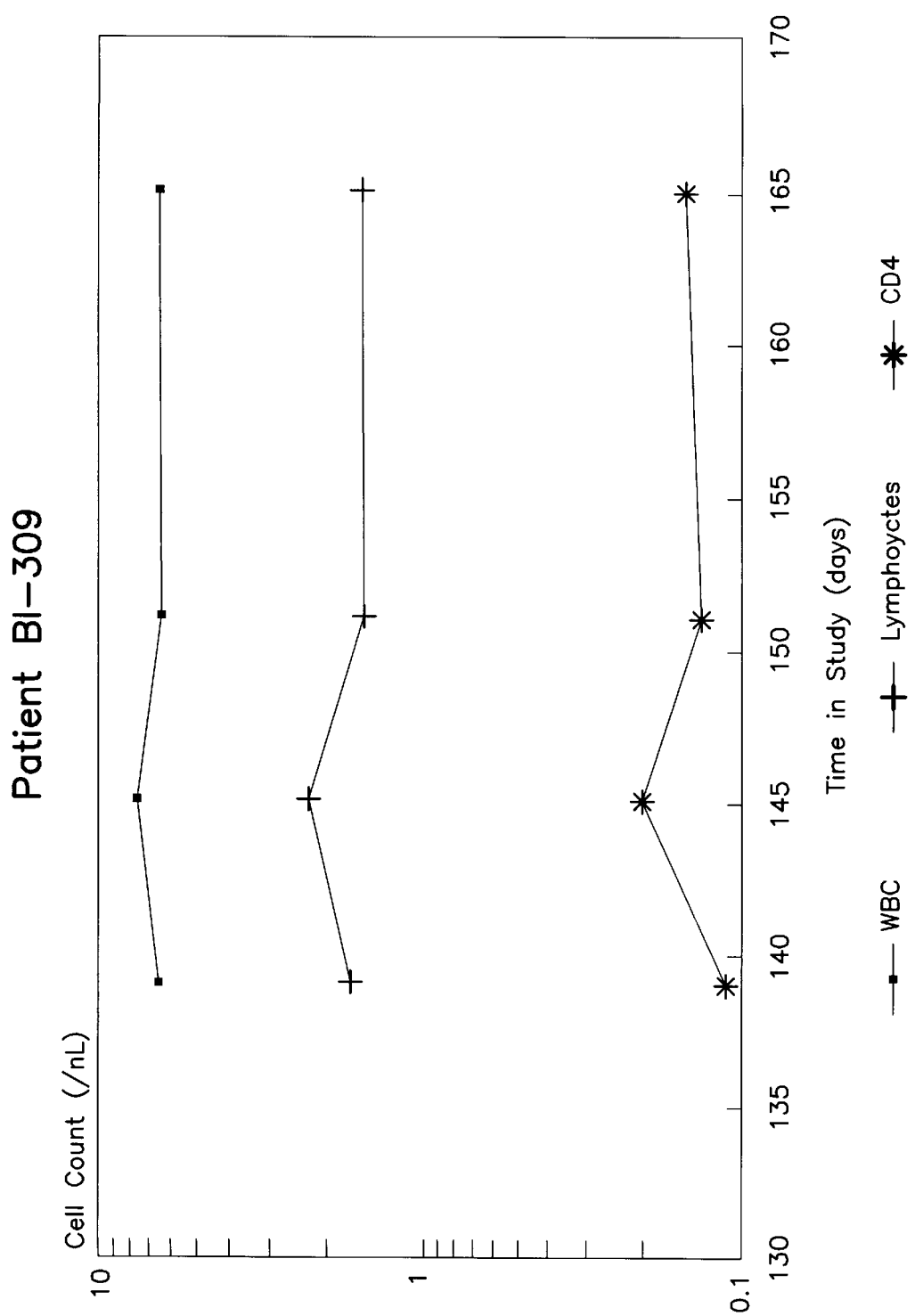
FIG. 3 is a graph showing white cell counts (including CD4+) versus time after enrollment of patient BI-309 in the study of intravenous anti-Rh$_o$(D) therapy.
Figure 4:
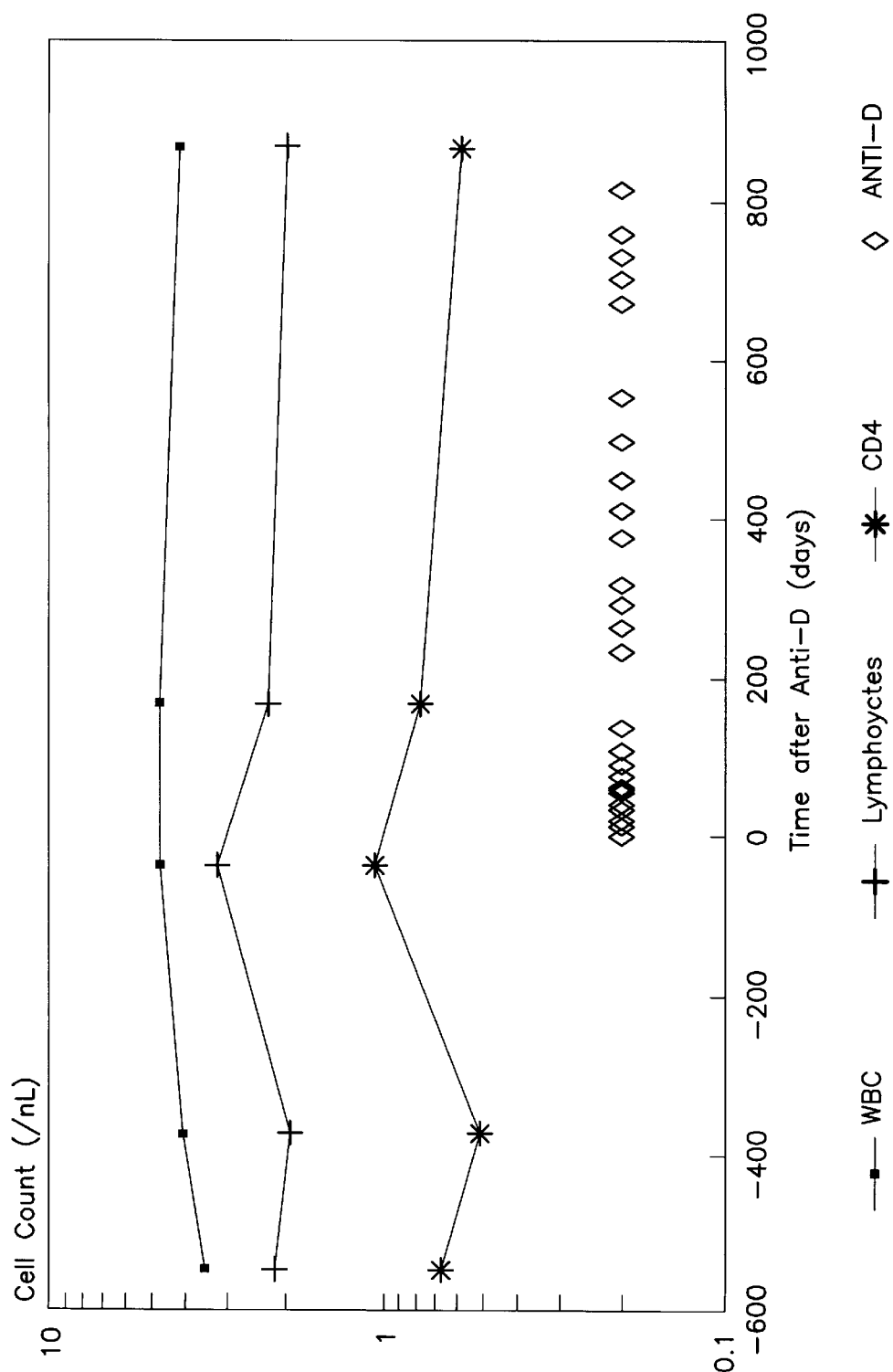
FIG. 4 is a graph showing white cell counts (including CD4+) versus time after enrollment of patient BI-57 in the study of intravenous anti-Rh$_o$(D) therapy.
Figure 5:
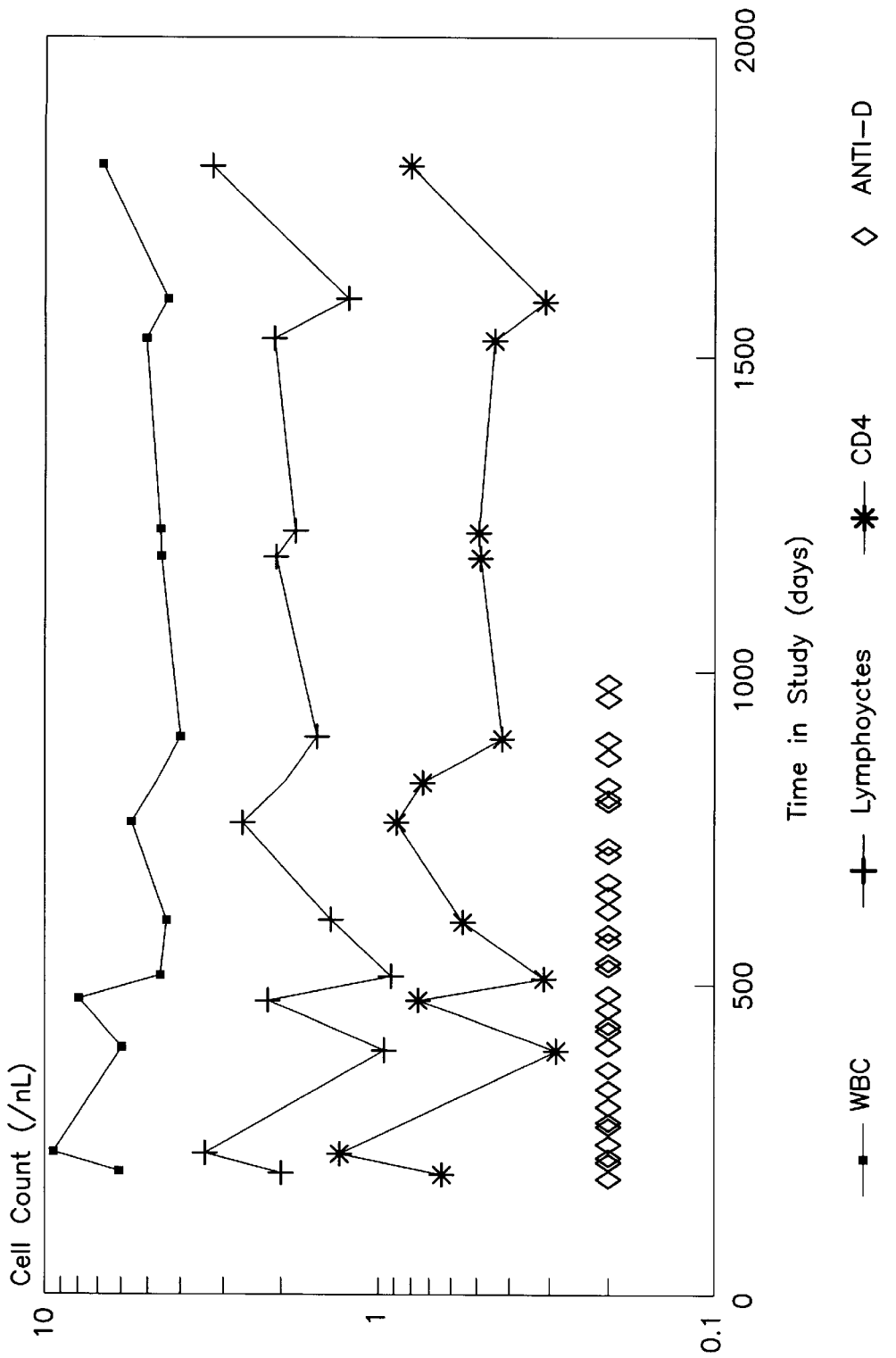
FIG. 5 is a graph showing white cell counts (including CD4+) versus time after enrollment of patient BI-33 in the study of intravenous anti-Rh$_o$(D) therapy.
Figure 6:
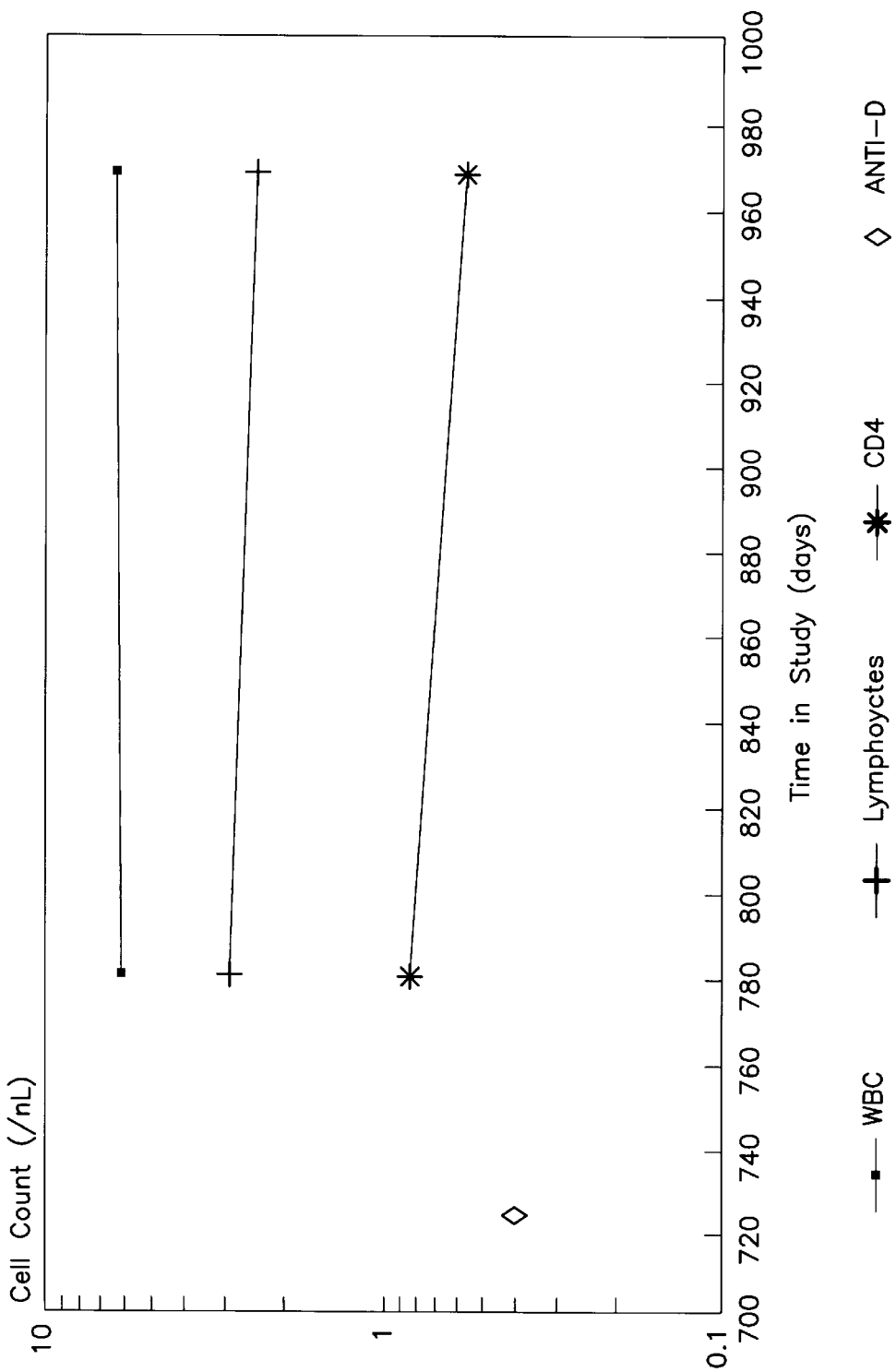
FIG. 6 is a graph showing white cell counts (including CD4+) versus time after enrollment of patient BI-77 in the study of intravenous anti-Rh$_o$(D) therapy.
Figure 7:
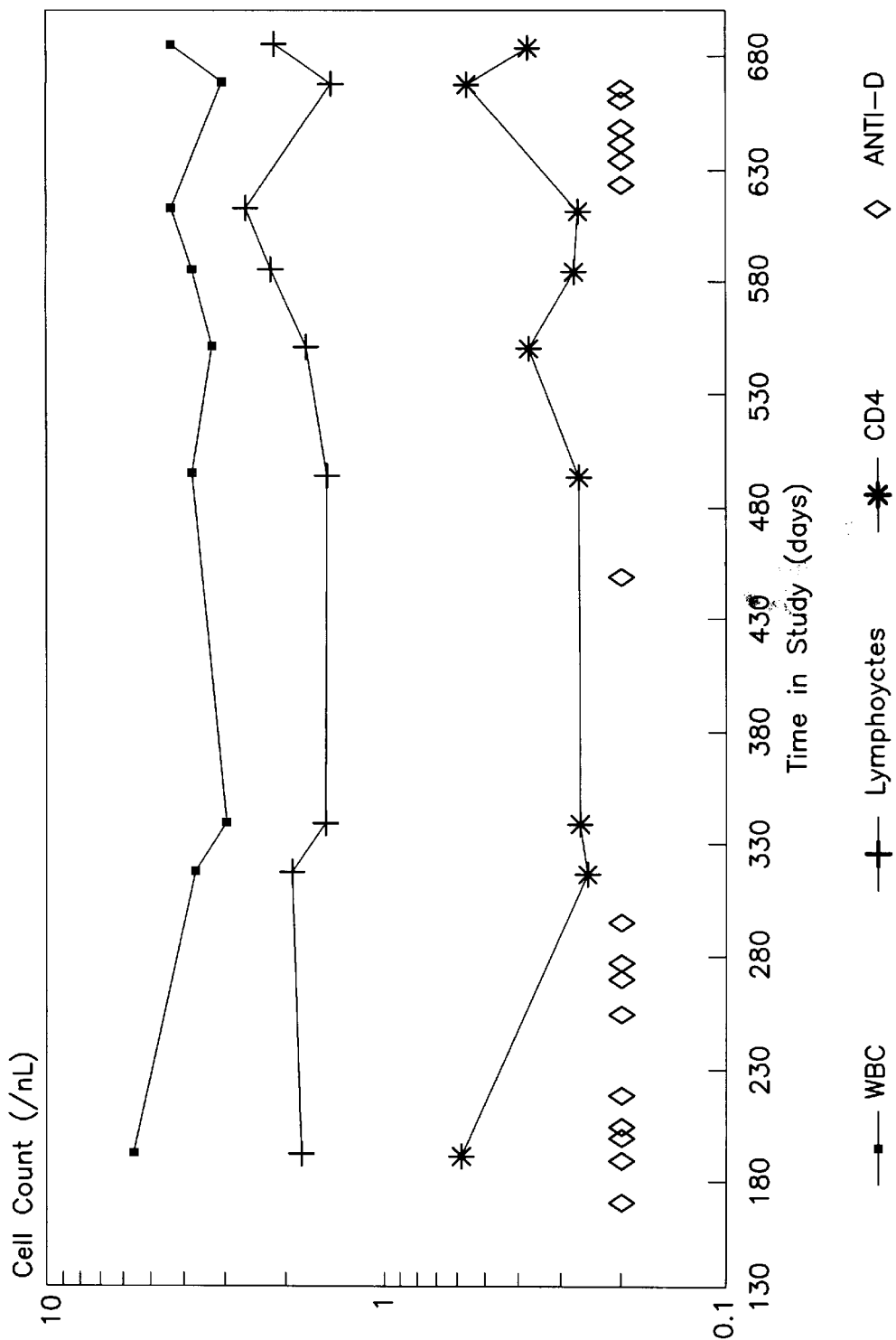
FIG. 7 is a graph showing white cell counts (including CD4+) versus time after enrollment of patient BI-101 in the study of intravenous anti-Rh$_o$(D) therapy.
Figure 8:
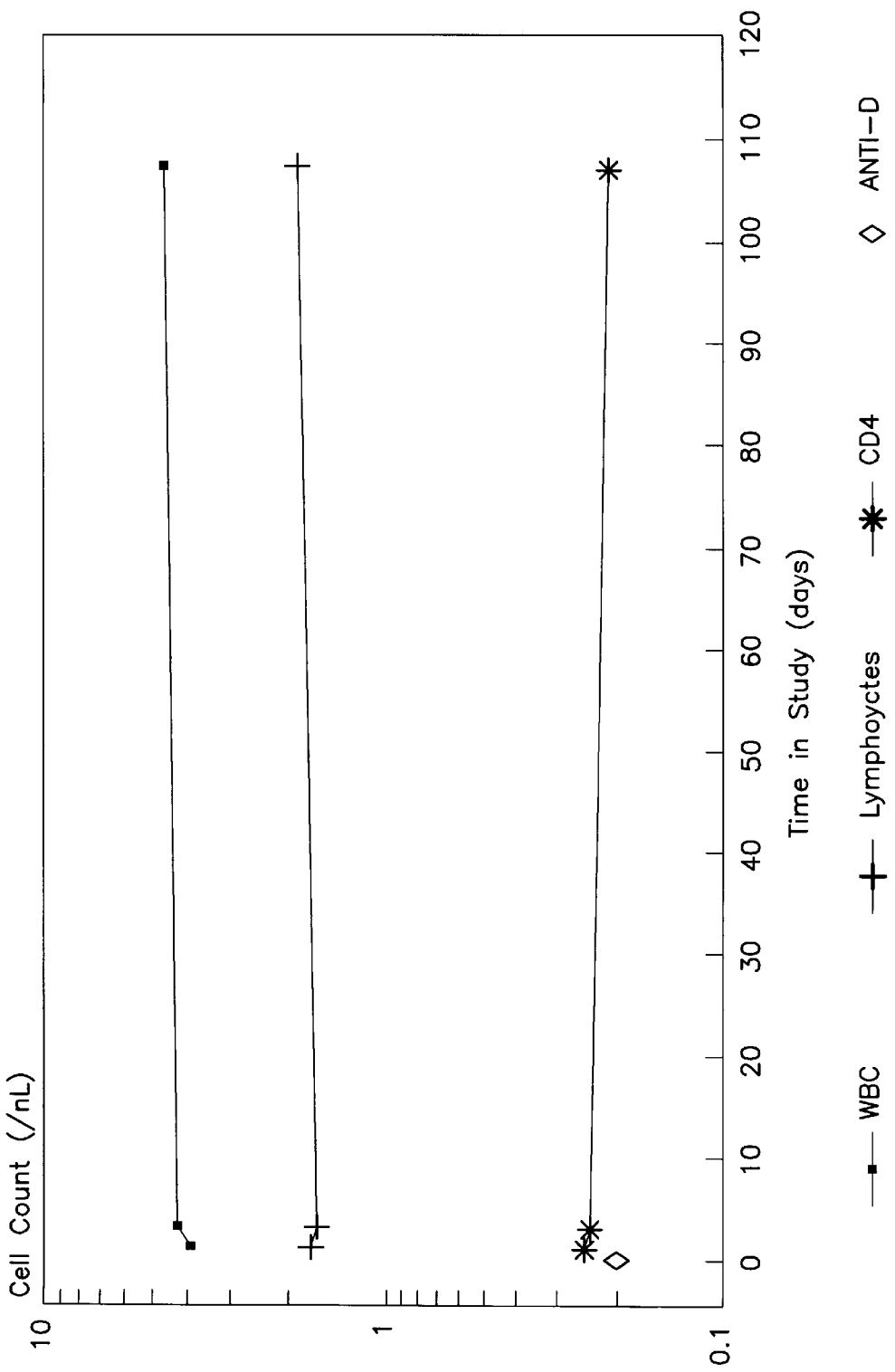
FIG. 8 is a graph showing white cell counts (including CD4+) versus time after enrollment of patient BI-154 in the study of intravenous anti-Rh$_o$(D) therapy.
Figure 9:
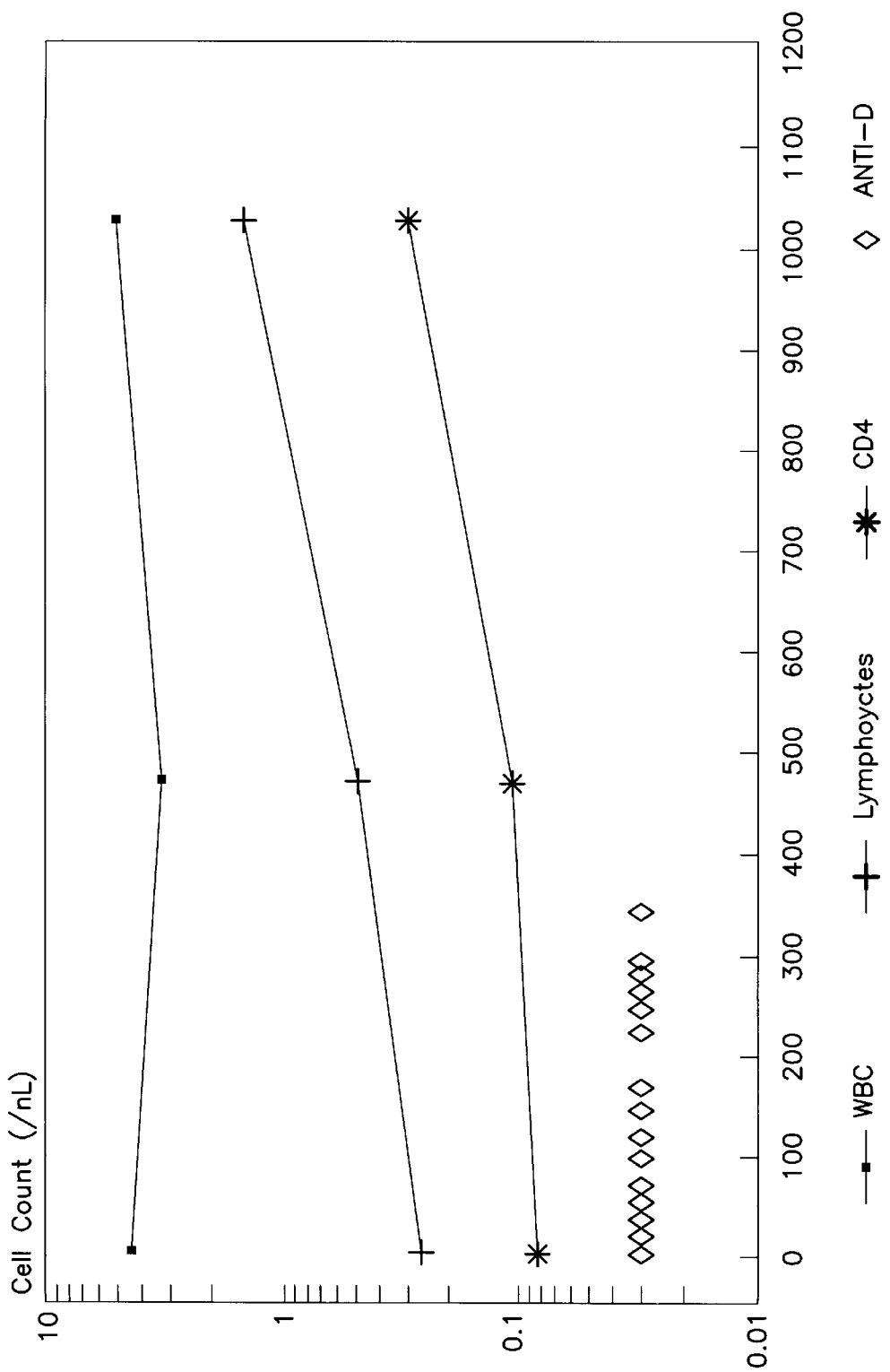
FIG. 9 is a graph showing white cell counts (including CD4+) versus time after enrollment of patient BI-117 in the study of intravenous anti-Rh$_o$(D) therapy.
Figure 10:
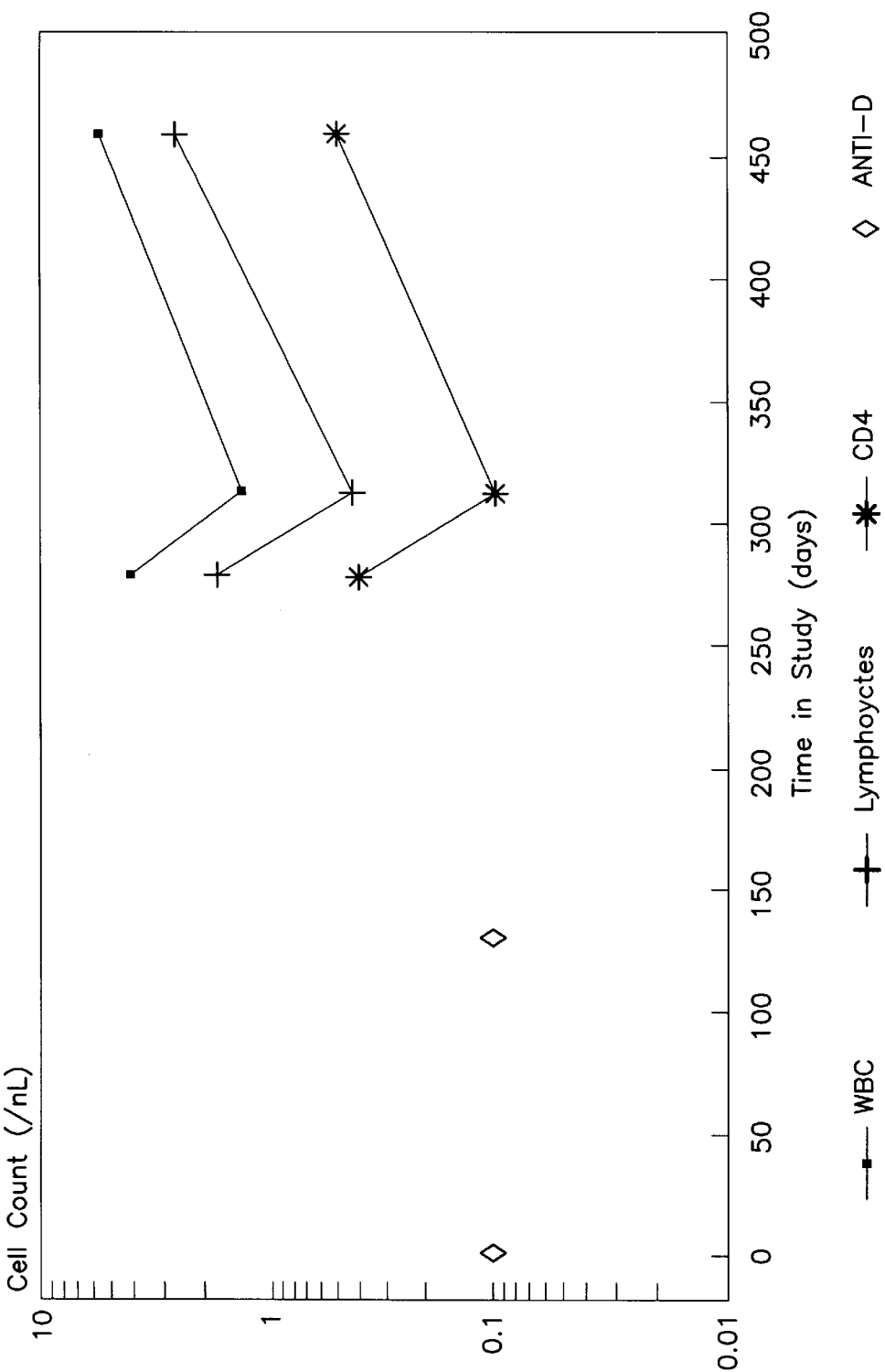
FIG. 10 is a graph showing white cell counts (including CD4+) versus time after enrollment of patient BI-139 in the study of intravenous anti-Rh$_o$(D) therapy.
Figure 11:
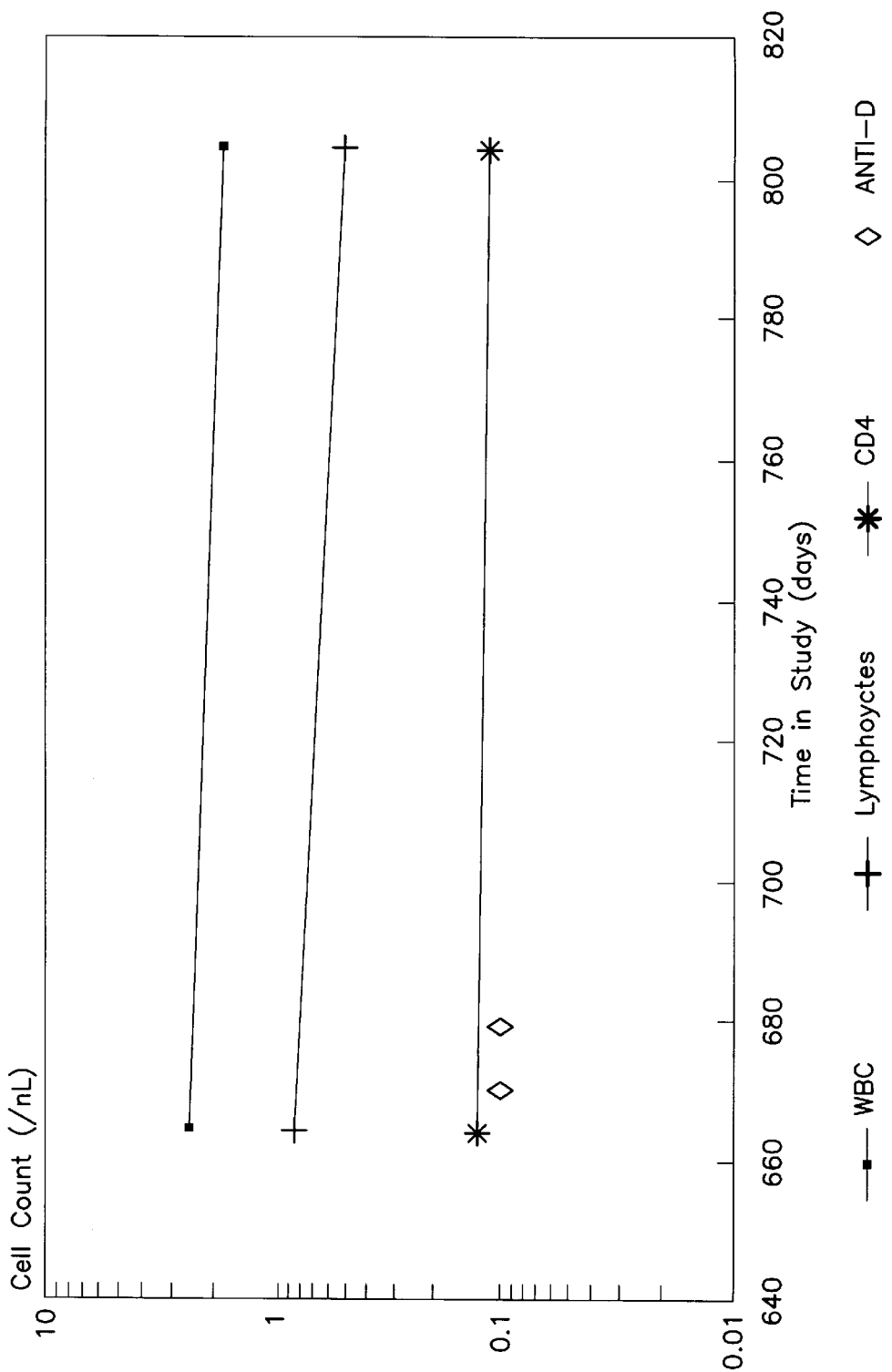
FIG. 11 is a graph showing white cell counts (including CD4+) versus time after enrollment of patient BI-146 in the study of intravenous anti-Rh$_o$(D) therapy.
Figure 12:
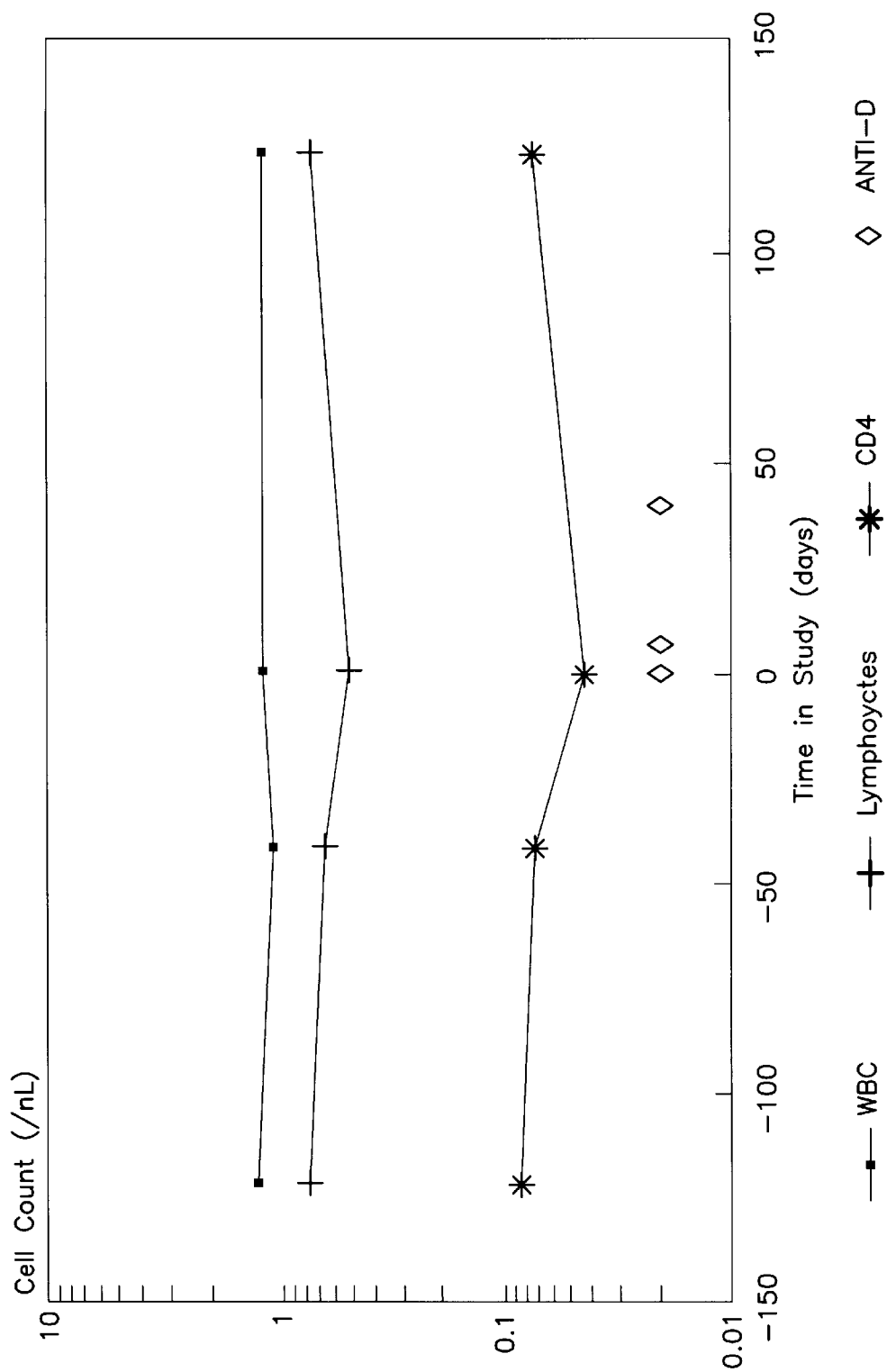
FIG. 12 is a graph showing white cell counts (including CD4+) versus time after enrollment of patient BI-301 in the study of intravenous anti-Rh$_o$(D) therapy.

The effect of an immunomodulatory therapy (Intravenous anti-D) upon immunocompromised patients, and available CD4 counts in these patients were examined. Table 1 and FIGS. 1 to 12 show data obtained from patients with ITP secondary to HIV infection and who had been treated with IV anti-D therapy (both WinRho® and WinRho SD®).

The data was supplemental data which was available on 12 patients who were enrolled in a clinical study of IV anti-D treatment of severe ITP. Table 1 shows patient ID, date of sample collection, white blood cell count, lymphocyte count (represented as a cell count and as a percentage of WBC) and CD4-positive lymphocyte count (represented as a cell count and as a percentage of lymphocytes). Cell counts are also presented relative to the enrollment of the patient into the study of IV anti-D therapy (FIGS. 1 to 12); times of anti-D therapy are also indicated in the Figures.

The CD4 marker is normally present on about 60% of peripheral T cells and T cells normally constitute 80–90% of the lymphocyte population. Therefore, CD4 markers are normally expected to be found on about 50% of lymphocytes. As would be expected of a HIV infected population, the CD4 population represented less than 50% of lymphocytes and a range of 7–40% of lymphocytes was observed. These differences in CD4 levels reflect the stages of the history of the HIV infections; while the higher CD4 counts occurred in patients with persistent generalized lymphadenopathy with constitutional symptoms; lower counts occurred in patients with AIDS-related complex, and AIDS.

The 12 patients were followed for 123–1801 days (mean 920±555 days; median 876 days) after initiating IV anti-D therapy. Despite the short life expectancy of this patient population, there were no deaths from AIDS-related illnesses in these patients during the study. In no instance has there been a death of an immunocompromised patient in a study with WinRho® or WinRho SD® that has been believed to be premature or related to anti-D therapy. Treatment with anti-D of the patients did not exacerbate the immune deficiency of the 12 patients who have been followed for about 3 years, and in some cases the patients have responded to therapy with increased CD4 cell counts.

Example 2

This example describes a treatment schedule for delaying HIV progression in asymptomatic HIV patients. $Rh_o(D)$-positive, non-splenectomized, patients with CD4+ T-lymphocyte counts of at least about 200 cells per $mm^3$ may be treated with multiple courses of intravenous WinRho SD. The courses are given at 3-week intervals, and each course consists of intravenous injections of about 25 microgram (ug) per kilogram (kg) per day WinRho SD for 2 consecutive days for a total of about 50 ug per kg per course. Antiviral response of WinRho SD treatment should be monitored throughout the treatment period by quantitative assessment of patient CD4+ T-lymphocyte count and HIV-1 viral load.

Intravenous WinRho SD therapy at this dosage would delay the progression of HIV-1 infection in asymptomatic HIV-1 infected patients. WinRho SD should increase patient CD4+ T-cell counts and decrease patient HIV-1 viral load over the course of treatment.

Example 3

This example describes a second treatment schedule for delaying HIV progression in asymptomatic HIV patients. $Rh_o(D)$-positive, non-splenectomized, patients with CD4+ T-lymphocyte counts of at least about 200 cells per $mm^3$ may be treated with multiple courses of subcutaneous anti-$Rh_oD$ immunoglobulin. The courses are given at 3-week intervals, and each course consists of subcutaneous injections of about 200 microgram (ug) per kilogram (kg) per day. Antiviral response of treatment should be monitored throughout the treatment period by quantitative assessment of patient CD4+ T-lymphocyte count and HIV-1 viral load.

In contrast to the intravenous dosing schedules as outlined in Examples 1 and 2, subcutaneous injection of anti-$Rh_oD$ immunoglobulin would produce significantly lower patient response rates with respect to the number of patients responding to treatment, increases in patient CD4+ T-lymphocyte count, and decreases in HIV-1 viral load.

Example 4

This example describes another patient treatment schedule similar to that described in Example 2 except that the WinRho SD dosage is substantially lower than 50 ug per kg per course. WinRho SD therapy at this low dose would not delay HIV disease progression as compared to the the high dosage regimen.

In a randomized 2-way crossover study, $Rh_o(D)$-positive patients who are non-splectomized and have entry CD4+ T-lymphocyte counts of at least about 200 cells per $mm^3$ will be given high and low doses of WinRho SD. The first patient group will receive 3 courses of high dose WinRho SD followed by 3 courses of low dose WinRho SD, while the second patient group will receive 3 courses of low dose WinRho SD followed by 3 courses of high dose WinRho SD. Each course of treatment will be given at 3-week intervals and consisted of intravenous administration of 25 or 0.25 ug/kg/day WinRho SD for 2 consecutive days for a total of 50 ug/kg/course and 0.50 ug/kg/course for the high dose and low dose regimens respectively. The two 3-course treatment cycles in each patient group are separated by a 6-week washout period.

Example 5

The removal of the spleen of HIV-infected patients has been shown to improve patient survival, increase absolute CD4+ and CD8+ T-cell counts, and delay the development of AIDS (Coyle, T. et al. *Am. J. Hematol.* 41:144–146 (1992); Tunkel, A. R. et al., *Am. J. Med. Sci.* 306: 105–110 (1993); Mientjes, G. et al., *AIDS* 8:269–271 (1994); Morlat, P. et al., *AIDS* 10:1172–1174 (1996)). However, it is predicted that anti-$Rh_oD$ immunoglobulin is ineffective in delaying HIV progression in splenectomized patients. As a protocol to support this prediction, multiple courses of WinRho SD at 50 ug or 0.5 ug per kg per course should be given at 3-week intervals to $Rh_o(D)$-positive, splenectomized, patients with CD4+ T-lymphocyte counts of at least about 200 cells per $mm^3$.

Example 6

The currently commercialized antiretroviral agents have limited efficacy in the pharmacologic containment of HIV infection, and antiretroviral therapy alone does not restore lost immune function. Nucleoside-based reverse transcriptase inhibitors are weak antiretroviral agents which can reduce HIV viral load by about 0.7 log. Non-nucleoside reverse transcriptase inhibitors are relatively stronger and can reduce viral load by 1.0 to 1.5 log. Novel inhibitors of HIV protease are presently the most effective agents and can reduce viral load by up to 2.0 log (Ho, D. D., *New Eng. J. Med.* 333:450–451 (1995)).

This example describes a protocol for assessing the synergistic activity of anti-$Rh_oD$ immunoglobulin with antiretroviral monotherapy or combinational therapy.

WinRhoSD can be administered intravenously to patients receiving more than one antiretroviral drugs from the following: (i) nucleoside reverse transcriptase inhibitors such as zidovudine, didanosine, zalcitabine, or stavudine; (ii) non-nucleoside reverse transcriptase inhibitors such as nevirapine, delavirdine, atevirdine, pyridinones or TIBO derivatives; and (iii) HIV protease inhibitors such as ritonavir, saquinavir, or indinavir. Dosage regimentation of intravenous WinRho SD is substantially as described in Examples 2 and 4. Effective therapeutic dosages of nucleoside reverse transcriptase inhibitors are about 500 to 600 milligram (mg) per day for Zidovudine, about 200 to 750 mg per day for didanosine, about 300 to 600 mg per day for lamivudine, about 2.25 mg per day for zalcitabine and about 5 to 150 mg per day for stavudine. Effective therapeutic dosages of the non-nucleoside reverse transcriptase inhibitors nevirapine and atevirdine are about 200 to 400 mg per day and about 50 to 300 mg per day, respectively. Effective therapeutic dosages of the HIV protease inhibitors saquinavir and ritonavir are about 1,800 mg per day and 1,200 mg per day, respectively.

Combinational therapy of anti-$Rh_oD$ immunoglobulin with antiretroviral agents would provide greater and more sustained effect in reducing HIV viral burden in the treatment of HIV infection than monotherapy. The extent of synergism may vary among different combinations. In general, synergism is maximal when anti-$Rh_oD$ immunoglobulin is combined with antiretroviral agents of different classes (e.g. WinRho SD with nucleoside reverse transcriptase inhibitor and protease inhibitor). When anti-$Rh_oD$ immunoglobulin is combined with antiretroviral agents from the same class (e.g. more than one nucleoside reverse transcriptase inhibitors), synergism is achieved when agents based on different nucleosides are combined (e.g. 3'-azidothymidine with 2',3'-dideoxyinosine or 2',3'-dideoxycytidine). Antagonism is achieved when agents based on the same nucleoside are combined (3'-azidothymidine with didehydrodideoxythymidine).

Example 7

This example describes a protocol for assessing the synergistic effect of anti-$Rh_oD$ immunoglobulin with alpha-interferon or human growth hormone in HIV-infected patients. Alpha-interferon is a family of cytokines with demonstrated immunomodulatory and antiviral properties. Its clinical utility in treating HIV-associated Kaposi's sarcoma has been established and it may also be useful in the treatment of HIV infection. Human growth hormone is an adenohypophyseal hormone with demonstrated clinical benefit in reversing progressive weight loss common in HIV infection. Major commercial products of alpha-interferon and human growth hormone are produced by recombinant DNA technology.

The combination of anti-$Rh_oD$ immunoglobulin with alpha-interferon in HIV-infected patients would produce synergistic effects in increasing patient CD4+ T-cell counts and decreasing HIV viral load. Effective dosage of intravenous WinRho SD is substantially as described in Examples 2 and 4. Effective dosage of alpha-interferon is about 1 to 15 million units (MU) per day given by subcutaneous or intramuscular injection.

The combination of anti-$Rh_oD$ immunoglobulin with human growth hormone is expected to produce a synergistic effect in reversing weight in AIDS patients. Patient CD4+ T-cell counts are increased and HIV viral load is decreased. Effective dosage of intravenous WinRho SD is substantially as described in Examples 2 and 4. Effective therapeutic dosage of human growth hormone for the treatment of AIDS-associated cachexia is about 0.18 to 0.38 mg or about 0.5 to 1.0 international units (IU) per week given by subcutaneous or intramuscular injection.

Having illustrated and described the principles of the invention in a preferred embodiment, it should be appreciated to those skilled in the art that the invention can be modified in arrangement and detail without departure from such principles. We claim all modifications coming within the scope of the following claims.

TABLE 1

| PATIENT | | WBC | Lymphocyte | | CD4 | |
|---|---|---|---|---|---|---|
| ID | DATE | $\times10^9$/L | % WBC | $\times10^9$/L | % Lymp | $\times10^9$/L |
| BI-101 | 90.09.25 | 5.60 | 32% | 1.79 | 32.6% | 0.58 |
| BI-101 | 91.01.29 | 3.70 | 52% | 1.92 | 13.4% | 0.26 |
| BI-101 | 91.02.20 | 3.00 | 51% | 1.53 | 17.4% | 0.27 |
| BI-101 | 91.07.25 | 3.80 | 40% | 1.52 | 17.8% | 0.27 |
| BI-101 | 91.09.20 | 3.30 | 53% | 1.75 | 21.4% | 0.37 |
| BI-101 | 91.10.23 | 3.80 | 59% | 2.24 | 12.4% | 0.28 |
| BI-101 | 91.11.20 | 4.40 | 60% | 2.64 | 21.7% | 0.57 |
| BI-101 | 92.01.14 | 3.10 | 47% | 1.46 | 23.6% | 0.34 |
| BI-101 | 92.01.31 | 4.40 | 50% | 2.20 | 17.2% | 0.38 |
| BI-107 | 87.10.06 | 5.10 | 54% | 2.75 | 29.4% | 0.81 |
| BI-107 | 88.03.01 | 7.00 | 44% | 3.08 | 33.6% | 1.03 |
| BI-107 | 89.01.20 | 6.30 | 56% | 3.53 | 32.9% | 1.16 |
| BI-107 | 89.08.01 | 5.10 | 49% | 2.50 | 31.0% | 0.77 |
| BI-107 | 89.10.20 | 6.30 | 44% | 2.77 | 31.9% | 0.88 |
| BI-107 | 89.10.28 | 6.10 | 47% | 2.87 | 31.9% | 0.91 |
| BI-107 | 89.11.17 | 6.60 | 51% | 3.37 | 29.9% | 1.01 |
| BI-107 | 90.04.27 | 6.80 | 24% | 1.63 | 13.8% | 0.23 |
| BI-107 | 90.08.17 | 7.80 | 56% | 4.37 | 26.0% | 1.14 |
| BI-107 | 91.02.01 | 7.20 | 62% | 4.46 | 24.7% | 1.10 |
| BI-107 | 91.08.22 | 6.10 | 28% | 1.71 | 35.1% | 0.60 |
| BI-117 | 88.05.19 | 4.40 | 6% | 0.26 | 31.6% | 0.08 |

TABLE 1-continued

| PATIENT ID | DATE | WBC ×10⁹/L | Lymphocyte % WBC | Lymphocyte ×10⁹/L | CD4 % Lymp | CD4 ×10⁹/L |
|---|---|---|---|---|---|---|
| BI-117 | 89.08.30 | 3.30 | 15% | 0.50 | 21.4% | 0.11 |
| BI-117 | 91.03.08 | 5.10 | 29% | 1.48 | 20.1% | 0.30 |
| BI-139 | 91.08.06 | 4.10 | 43% | 1.76 | 23.3% | 0.41 |
| BI-139 | 91.09.10 | 1.36 | 32% | 0.44 | 22.7% | 0.10 |
| BI-139 | 92.02.03 | 5.60 | 48% | 2.69 | 20.5% | 0.55 |
| BI-146 | 92.04.09 | 2.50 | 34% | 0.85 | 15.0% | 0.13 |
| BI-146 | 92.08.25 | 1.80 | 28% | 0.50 | 22.0% | 0.11 |
| BI-154 | 90.06.28 | 3.90 | 44% | 1.72 | 14.5% | 0.25 |
| BI-154 | 90.06.30 | 4.25 | 39% | 1.66 | 14.5% | 0.24 |
| BI-154 | 90.10.12 | 4.60 | 41% | 1.89 | 11.2% | 0.21 |
| BI-21 | 89.06.20 | 3.70 | 42% | 1.55 | 12.3% | 0.19 |
| BI-21 | 89.09.01 | 3.20 | 53% | 1.70 | 19.4% | 0.33 |
| BI-21 | 90.01.23 | 3.30 | 41% | 1.35 | 18.0% | 0.24 |
| BI-21 | 90.02.06 | 2.80 | 50% | 1.40 | 17.3% | 0.24 |
| BI-21 | 90.06.26 | 2.30 | 54% | 1.24 | 7.1% | 0.09 |
| BI-21 | 91.03.27 | 2.50 | 64% | 1.60 | 15.3% | 0.24 |
| BI-21 | 91.04.16 | 2.40 | 29% | 0.70 | 19.1% | 0.13 |
| BI-21 | 91.04.23 | 2.90 | 36% | 1.04 | 15.1% | 0.16 |
| BI-21 | 91.05.14 | 2.50 | 58% | 1.45 | 18.6% | 0.27 |
| BI-21 | 91.05.30 | 2.40 | 68% | 1.63 | 13.9% | 0.23 |
| BI-21 | 91.07.23 | 3.00 | 52% | 1.56 | 15.6% | 0.24 |
| BI-21 | 92.01.07 | 2.90 | 51% | 1.48 | 11.6% | 0.17 |
| BI-21 | 92.03.30 | 2.80 | 55% | 1.54 | 20.1% | 0.31 |
| BI-301 | 91.10.17 | 1.26 | 61% | 0.77 | 11.0% | 0.08 |
| BI-301 | 92.02.13 | 1.10 | 60% | 0.66 | 11.0% | 0.07 |
| BI-301 | 92.03.27 | 1.20 | 43% | 0.52 | 8.4% | 0.04 |
| BI-301 | 92.07.28 | 1.21 | 62% | 0.75 | 10.0% | 0.08 |
| BI-309 | 92.06.03 | 6.50 | 26% | 1.69 | 6.7% | 0.11 |
| BI-309 | 92.06.09 | 7.60 | 30% | 2.28 | 8.9% | 0.20 |
| BI-309 | 92.06.15 | 6.40 | 24% | 1.54 | 8.8% | 0.14 |
| BI-309 | 92.06.29 | 6.50 | 24% | 1.56 | 9.6% | 0.15 |
| BI-33 | 88.02.28 | 6.10 | 33% | 2.01 | 31.8% | 0.64 |
| BI-33 | 88.03.29 | 9.40 | 36% | 3.38 | 38.6% | 1.31 |
| BI-33 | 88.09.14 | 6.00 | 16% | 0.96 | 30.6% | 0.29 |
| BI-33 | 88.11.29 | 7.90 | 28% | 2.21 | 34.8% | 0.77 |
| BI-33 | 89.01.06 | 4.60 | 20% | 0.92 | 34.3% | 0.32 |
| BI-33 | 89.04.04 | 4.40 | 32% | 1.41 | 39.6% | 0.56 |
| BI-33 | 89.09.12 | 5.60 | 47% | 2.63 | 34.0% | 0.90 |
| BI-33 | 89.11.14 | 4.70 | 42% | 1.97 | 37.7% | 0.74 |
| BI-33 | 90.01.23 | 4.00 | 39% | 1.56 | 27.4% | 0.43 |
| BI-33 | 90.11.08 | 4.60 | 46% | 2.12 | 23.7% | 0.50 |
| BI-33 | 90.12.20 | 4.60 | 40% | 1.84 | 27.5% | 0.51 |
| BI-33 | 91.10.17 | 5.10 | 42% | 2.14 | 20.8% | 0.45 |
| BI-33 | 91.12.18 | 4.40 | 29% | 1.28 | 25.1% | 0.32 |
| BI-33 | 92.07.22 | 6.80 | 48% | 3.26 | 25.0% | 0.82 |
| BI-57 | 87.08.03 | 3.50 | 62% | 2.17 | 17.0% | 0.37 |
| BI-57 | 88.01.25 | 4.10 | 48% | 1.97 | 26.0% | 0.51 |
| BI-57 | 88.12.27 | 4.70 | 48% | 3.20 | 33.0% | 1.05 |
| BI-57 | 89.07.18 | 4.70 | 48% | 2.26 | 34.0% | 0.77 |
| BI-57 | 91.06.19 | 4.10 | 48% | 1.97 | 29.0% | 0.57 |
| BI-77 | 91.07.25 | 6.10 | 48% | 2.93 | 28.6% | 0.84 |
| BI-77 | 92.01.29 | 6.30 | 39% | 2.46 | 23.2% | 0.57 |

We claim:

1. A method for stabilizing CD4 cell counts in a subject who is exposed to HIV, or infected by HIV, comprising administering an amount of anti-Rh$_o$(D) antibodies sufficient to stabilize CD4 cell counts.

2. A method as claimed in claim 1 wherein the subject is Rh positive.

3. A method according to claim 1 wherein the anti-Rh$_o$(D) antibodies are administered intravenously in a dose of about 10–200 μg per kg body weight.

4. A method according to claim 3 where in the anti-Rh$_o$(D) antibodies are administered intravenously in a dose of at least 25 μg per kg body weight.

5. A method according to claim 1 wherein the anti-Rh$_o$(D) antibodies are administered intramuscularly in a dose of at least 20–400 μg per kg body weight.

6. A method as claimed in claim 1 wherein the subject has a CD4+ cell count above 200 cells per mm$^3$.

7. A method as claimed in claim 1 wherein the subject is under remission from thrombocytopenia secondary to HIV infection.

8. A method according to claim 1, wherein the anti-Rh$_o$(D) antibodies are human anti-Rh$_o$(D) immunoglobulin.

9. A method according to claim 1, wherein the anti-Rh$_o$(D) antibodies are recombinant human anti-Rh$_o$(D) immunoglobulin.

10. A method according to claim 1 wherein the subject is non-splenectomized.

11. A method according to claim 1, wherein the anti-Rh$_o$(D) antibodies are polyclonal anti-Rh$_o$(D) immune globulin prepared from mammalian plasma or serum.

12. A method according to claim 1, wherein the anti-Rh$_o$(D) antibodies are monoclonal antibodies.

13. A method according to claim 1, wherein the subject suffers from immune thrombocytopenia purpura.

* * * * *